(12) United States Patent
Neupert et al.

(10) Patent No.: US 8,003,686 B2
(45) Date of Patent: Aug. 23, 2011

(54) ARYL DERIVATIVES OF CURCUMIN, DEMETHOXYCURCUMIN, BISDEMETHOXYCURCUMIN OR CURCUMINISOXAZOLIDE AND THEIR USE AS ANIMAL FEED ADDITIVES

(75) Inventors: Werner Neupert, Rheinfelden (DE); Aurelia Seon, Mulhouse (FR); Carlos Simoes-Nunes, Village-Neuf (FR); Christof Wehrli, Witterswil (CH)

(73) Assignee: DSM IP Assets B.V., TE Heerlen (NL)

( * ) Notice: Subject to any disclaimer, the term of this patent is extended or adjusted under 35 U.S.C. 154(b) by 370 days.

(21) Appl. No.: 11/919,581

(22) PCT Filed: Apr. 20, 2006

(86) PCT No.: PCT/EP2006/003603
§ 371 (c)(1),
(2), (4) Date: Mar. 21, 2008

(87) PCT Pub. No.: WO2006/117077
PCT Pub. Date: Nov. 9, 2006

(65) Prior Publication Data
US 2010/0010232 A1    Jan. 14, 2010

(30) Foreign Application Priority Data
May 3, 2005   (EP) .................................... 05009662

(51) Int. Cl.
*A61K 31/335* (2006.01)
*C07C 69/76* (2006.01)
(52) U.S. Cl. ............. 514/449; 514/378; 514/506; 560/8
(58) Field of Classification Search .................. 514/449, 514/378, 506; 560/8
See application file for complete search history.

(56) References Cited

FOREIGN PATENT DOCUMENTS

WO    WO 2004/031122       *  4/2004
WO    WO 2004/031122 A1 *  4/2004

OTHER PUBLICATIONS

Devi et al., Current Science, 2004, 87(10): 1324-1325.*
Selvam et al., Bioorganic & Medicinal Chemistry Letters, 2005, 15:1793-1797.*
Sui et al., 1995, CAS: 122:23248.*
Qiao et al., Journal Lab. Clin. Med., 1997, 130(6):576 (Abstract only).*
Patent Abstracts of Japan, vol. 1998, No. 10, Aug. 31, 1998 & JP 10 114647 A, May 6, 1998.
Pedersen et al, "Synthesis of Naturally Occurring Curcuminoids and Related Compounds", Liebigs Annalen Der Chemie, Verlag Chemie, GMBH, Weinheim, DE, 1985, pp. 1557-1569.
Milobedzka et al, "Zur Kenntnis des Curcumins", Ber. Deutsch. Chem. Gessellschaft, vol. 43, 1910, pp. 2163-2170.
Ireson et al, "Characterization of Metabolites of the Chemopreventive Agent Curcumin in Human and Rate Hepatocytes and in the Rat in Vivo, and Evaluation of Their Ability to Inhibit Phorbol Ester-induced Prostaglandin E2 Production", Cancer Research, American Association for Cancer Research, Baltimore, MD, US, vol. 61, No. 3, Feb. 1, 2001.
Selvam et al, "Desig, synthesis, biological evaluation and molecular docking of curcumin analogues as antioxidant, cyclooxygenase inhibitory and anti-inflammatory agents", Bioorganic & Medicinal Chemistry Letters, Oxford, GB, vol. 15, No. 7, Apr. 1, 2005, pp. 1793-1797.
Sui et al, "Inhibition of the HIV-1 and HIV-2 Proteases by Curcumin and Curcumin Boron Complexes", Bioorganic & Medicinal Chemistry, vol. 1, No. 6, 1993, pp. 415-422.
Database CAPLUS Chemical Abstracts Service, Columbus, Ohio, US; XP002397849 & h. Qizhi et al, "High-performance liquid chromatography of complex derived from boron and curcumin and its application", Fenxi Huaxue, vol. 23, No. 3, 1995, pp. 314-316.
& v. Lampe et al, "Synthesis of p,p'-dihydroxydicinnamylmethane" Berichte Der Deutschen Chemischen Gesselschaft, vol. 51, 1918, pp. 1355-1360.
International Search Report mailed Sep. 9, 2006 in PCT/EP2006/003603.
Written Opinioni mailed Sep. 9, 2006 in PCT/EP2006/003603.

* cited by examiner

*Primary Examiner* — Rei-tsang Shiao
(74) *Attorney, Agent, or Firm* — Nixon & Vanderhye P.C.

(57) ABSTRACT

The present invention relates to the use of acyl derivatives of curcumin, desmethoxy curcumin and bisdesmethoxy curcumin and of curcuminisoxazolide as components of animal feed or feed additives for the improvement of animal performance and the new acyl derivatives per se as well as the corresponding animal feed or feed additives containing them.

18 Claims, No Drawings

ARYL DERIVATIVES OF CURCUMIN, DEMETHOXYCURCUMIN, BISDEMETHOXYCURCUMIN OR CURCUMINISOXAZOLIDE AND THEIR USE AS ANIMAL FEED ADDITIVES

This application is the US national phase of international application PCT/EP2006/003603 filed 20 Apr. 2006 which designated the U.S. and claims benefit of EP 05009662.7, dated 3 May 2005, the entire content of which is hereby incorporated by reference.

The present invention relates to curcumin derivatives and their use. More precisely, the present invention relates to the use of new and known acyl derivatives of curcumin, desmethoxycurcumin and bisdesmethoxycurcumin and of curcuminisoxazolide as components of animal feed or feed additives, as well as to new acyl derivatives of curcumin, desmethoxycurcumin and bisdesmethoxycurcumin themselves and to compositions, feed additives and feed containing them.

Curcumin, desmethoxycurcumin and bisdesmethoxycurcumin are known, naturally occurring compounds which exhibit different biological activities, such as antioxidative, anti-inflammatory, antiviral and anticancerogenous activities.

WO 2004/031122 A1 discloses novel curcumin and tetrahydrocurcumin derivatives for use in cosmetics, pharmaceuticals and for nutrition. The novel derivatives are said to be especially suitable as radical interceptors, for the care and protection of skin, especially sensitive skin and skin which has aged or is ageing as a result of intrinsic and/or extrinsic factors, for the treatment and prophylaxis of cosmetic or dermatological skin alterations such as seborrheic signs, prominent proliferations and unwanted pigmentation (hyperpigmentation and hypopigmentation), for the prophylaxis and/or treatment of inflammatory skin diseases, e.g. psoriasis, and for the prophylaxis and/or treatment of cancer.

As discussed in WO 2004/031122 A1 (p. 5) curcumin and formulations thereof have been suggested for different users as food additives, anti-aging and other preparations for the treatment of human diseases. However, it has also been noted that orally applied curcumin on the one hand has a low activity in humans due to its low solubility and on the other hand also with respect to the production of pharmaceutical and cosmetic preparations its low solubility is a problem. Finally, curcumin has been found to be relatively unstable under physiological conditions. In accordance with the disclosure of WO 2004/031122 these drawbacks are overcome by the use of curcumins in pharmaceutical and cosmetic preparations or as food and feed additives in form of their mono- and diesters with organic acids. Organic acids which are suitable for these uses are saturated or unsaturated mono or polycarboxylic acids with a linear or branched chain of 1 to 30 carbon atoms, preferably fatty acids with 11, 14, 16 or 18 carbon atoms. Disclosed as especially useful are hydroxylated fatty acids such as 9-hydroxy-10-trans-12-cis-octadienoic acid and 13-hydroxy-10-trans-12-cis-octadienoic acid.

The compounds disclosed in WO 2004/031122 A1 are suitable for topical applications and on the other hand characterized by a higher stability against hydrolysis. Depending upon the nature of the acyl residue these compounds show higher lipophilic or hydrophilic activities than the basic curcumins. They are especially useful for topical applications in cosmetics and pharmaceutical preparation for the treatment of skin as already mentioned above.

An objective of the present invention was to find new curcumin derivatives with advantageous properties relative to curcumin and its analogs (desmethoxycurcumin and bisdesmethoxycurcumin) and to already known acyl derivatives thereof. In view of the constantly increasing requests for a ban of antibiotics in animal feed and a corresponding demand of compounds capable to replace antibiotics in animal feed and feed additives this objective included the identification of curcumin derivatives which could be used as substitutes for antibiotics. A further objective was to find advantageous new uses of already known and novel curcumine derivatives.

These objectives are accomplished by the present invention.

The present invention provides the use of curcuminisoxazolide and of acyl derivatives of curcumin, desmethoxycurcumin and bisdemethoxycurcumin as components of animal feed or feed additives wherein these derivatives are of the formula

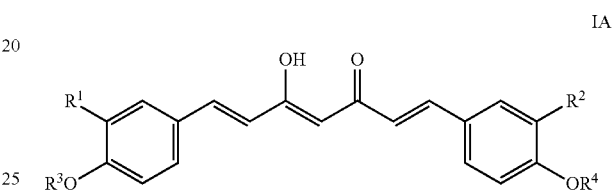

IA wherein
$R^1$ and $R^2$ are different or the same and represent hydrogen or methoxy;
$R^3$ and $R^4$ are different or the same and at least one of them is an acyl residue selected from
  (a) sulfuric and phosphoric acid and salts thereof;
  (b) an aliphatic, aromatic or araliphatic organic acid;
  (c) formula —CO—OR$^5$,
    with $R^5 = C_{1-6}$-alkyl;
  (d) formula —CO—(CH$_2$)p-R$^6$, —CO—(CH$_2$)$_q$—N$^+$(R$^8$)$_3$Y$^-$, —CO—(CH$_2$)$_q$—NH—COR$^9$ or —CO—NH—(CH$_2$)$_q$—COOR$^5$,
    with p=0 or 1,
    q=an integer of 1-6,
    Y$^-$=an anion of an inorganic acid,
    $R^6$=—NHR$^7$, —NR$^5$R$^7$, —CH(OH)R$^5$ or —CH(OR$^9$)R$^5$,
    $R^7$=H or $C_{1-6}$-alkyl,
    $R^8$=H or $C_{1-4}$-alkyl,
    $R^9 = C_{1-5}$-alkanoyl or
  (e) formula —CO—NH—(CH$_2$)$_q$—R$^{10}$,
    with $R^{10}$=H, $C_{1-6}$-alkyl or —COOC$_{1-6}$-alkyl
the other being hydrogen if only one of R$^3$ and R$^4$ is acyl;
of the formula A

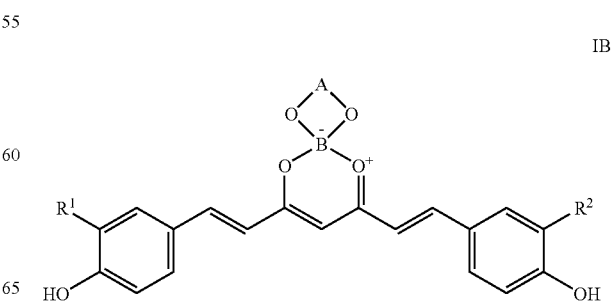

IB wherein
A is a group —CO—CHR$^9$—CO— or —CR$^{10}$R$^{11}$—CO—
  with R$^9$=H or C$_{1-4}$-alkyl,
    R$^{10}$=H and
    R$^{11}$=H, C$_{1-12}$-alkyl, —[CH(OH)]$_n$—CH$_2$OH, —(CH$_2$)$_m$—COOH, —(CH$_2$)$_m$-phenyl or —CH(OH)—COOH,
  or R$^{10}$=R$^{11}$=—CH$_2$—COOH
  or R$^{10}$+R$^{11}$=oxygen and
    n and m=integers of 0-4; or
of the formula 7

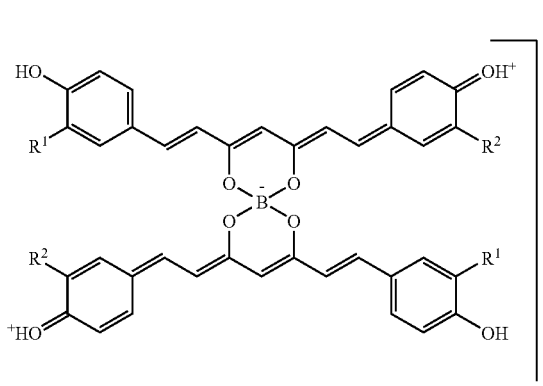

IC wherein R$^1$ and R$^2$ are as defined above and X$^-$=OH$^-$, Cl$^-$ or HSO$_4^-$;
or the use of these derivatives for the preparation of compositions improving the performance of animals, especially having activity as modulators of the gastrointestinal microflora and which are applicable via animal feed.

In specific embodiments of this aspect of the invention the acyl derivatives are of formula IA
  wherein R$^1$ and R$^2$ are methoxy;
  wherein one of R$^1$ and R$^2$ is methoxy and the other is hydrogen;
  wherein R$^1$ and R$^2$ are hydrogen;
  wherein R$^3$ and R$^4$ are the same;
  wherein at least one of R$^3$ and R$^4$ represents an acyl residue selected from group (a);
  wherein at least one of R$^3$ and R$^4$ represents an acyl residue selected from group (b);
  wherein at least one of R$^3$ and R$^4$ represents an acyl residue selected from group (c);
  wherein at least one of R$^3$ and R$^4$ represents an acyl residue of formula —CO—(CH$_2$)$_p$—R$^6$ of group (d);
  wherein at least one of R$^3$ and R$^4$ represents an acyl residue of formula —CO—(CH$_2$)$_p$—NHR$^7$ of group (d);
  wherein at least one of R$^3$ and R$^4$ represents an acyl residue of formula —CO—(CH$_2$)$_p$—NR$^5$R$^7$ of group (d);
  wherein at least one of R$^3$ and R$^4$ represents an acyl residue of formula —CO—(CH$_2$)$_p$—CH(OH)R$^5$ of group (d);
  wherein at least one of R$^3$ and R$^4$ represents an acyl residue of formula —CO—(CH$_2$)$_p$—CH(OR$^9$)R$^5$ of group (d);
  wherein at least one of R$^3$ and R$^4$ represents an acyl residue of formula —CO—(CH$_2$)$_q$—N$^+$(R$^8$)$_3$Y$^-$ of group (d);
  wherein at least one of R$^3$ and R$^4$ represents an acyl residue of formula —CO—(CH$_2$)$_q$—NH—COR$^9$ of group (d);
  wherein at least one of R$^3$ and R$^4$ represents an acyl residue of formula —CO—NH—(CH$_2$)$_q$—COOR$^5$ of group (d);
  wherein at least one of R$^3$ and R$^4$ represents an acyl residue of formula —CO—NH—(CH$_2$)$_q$H of group (e);
  wherein at least one of R$^3$ and R$^4$ represents an acyl residue of formula —CO—NH—(CH$_2$)$_q$—C$_{1-6}$-alkyl of group (e);
  wherein at least one of R$^3$ and R$^4$ represents an acyl residue of formula —CO—NH—(CH$_2$)$_q$—COOC$_{1-6}$-alkyl of group (e);
of formula IB
  wherein A is a group —CO—CHR$^9$—CO—;
  wherein A is a group —CR$^{10}$R$^{11}$—CO;
  wherein R$^{10}$ and R$^{11}$ are each —CH$_2$—COOH;
  wherein R$^{10}$ and R$^{11}$ taken together are oxygen; or
of formula IC.

In a further aspect the present invention provides new acyl derivatives of curcumins (which term as used hereinbelow comprises curcumin, desmethoxycurcumin and bisdesmethoxycurcumin unless explicitly stated otherwise) of formula

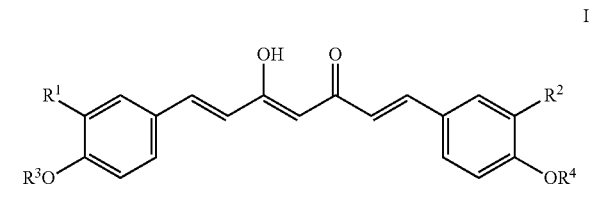

I wherein
R$^1$ and R$^2$ are different or the same and represent hydrogen or methoxy;
R$^3$ and R$^4$ are different or the same and at least one of them is an acyl residue selected from
  (a) phosphoric acid and salts thereof,
  (b) an amino acid, a hydroxy-C$_{3-6}$aliphatic acid or an aromatic or araliphatic acid;
  (c) formula —CO—OR$^5$
    with R$^5$=C$_{1-6}$-alkyl or
  (d) formula —CO—(CH$_2$)$_p$—R$^6$, —CO—(CH$_2$)$_q$—N$^+$(R$^8$)$_3$Y$^-$, —CO—(CH$_2$)$_q$—NH—COR$^9$ or —CO—NH—(CH$_2$)$_q$—COOR$^5$,
    with p=0 or 1,
    q=an integer of 1-6,
    Y$^-$=an anion of an inorganic acid,
    R$^6$=—NHR$^7$, —NR$^5$R$^7$, —CH(OH)R$^5$ or —CH(OR$^9$)R$^5$,
    R$^7$=H or C$_{1-6}$-alkyl,
    R$^8$=H or C$_{1-4}$-alkyl,
    R$^9$=C$_{1-5}$-alkanoyl or
  (e) formula —CO—NH—(CH$_2$)$_q$—R$^{10}$,
    with R$^{10}$=H, C$_{1-6}$-alkyl or COOC$_{1-6}$-alkyl,
  the other being hydrogen if only one of R$^3$ and R$^4$ is acyl;
with the proviso that when R$^1$ and R$^2$ are both methoxy R$^3$ and/or R$^4$ are not methoxycarbonyl, ethoxycarbonyl, glycyl, benzoyl or nicotinoyl.

Specific embodiments of this aspect of the invention are acyl derivatives of curcumins of formula I
  wherein at least one of R$^3$ and R$^4$ represents an acyl residue selected from group (a);
  wherein at least one of R$^3$ and R$^4$ represents an acyl residue selected from group (b), with the proviso that when R$^1$ and R$^2$ are both methoxy, R$^3$ and/or R$^4$ are not glycyl, benzoyl or nicotinoyl;
  wherein at least one of R$^3$ and R$^4$ represents an acyl residue of a hydroxy —C$_{3-6}$-aliphatic acid, wherein at least one of $R^3$ and $R^4$ represents an acyl residue of an amino acid with at least three carbon atoms, herein at least one of $R^3$ and $R^4$ represents an acyl residue of an aromatic acid, with the proviso that when $R^1$ and $R^2$ are both methoxy, $R^3$ and/or $R^4$ are not benzoyl or nicotinoyl;

wherein at least one of $R^3$ and $R^4$ represents an acyl residue of an araliphatic acid;

wherein at least one of $R^3$ and $R^4$ represents an acyl residue selected from group (c), with the proviso that when $R^1$ and $R^2$ are both methoxy, $R^3$ and $R^4$ are not methoxycarbonyl or ethoxycarbonyl;

wherein at least one of $R^3$ and $R^4$ represents an acyl residue of formula —CO(CH$_2$)$_p$—R$^6$;

wherein at least one of $R^3$ and $R^4$ represents an acyl residue of formula —CO—(CH$_2$)$_p$—NHR$^7$ of group (d);

wherein at least one of $R^3$ and $R^4$ represents an acyl residue of formula —CO—(CH$_2$)$_p$—NR$^5$R$^7$ of group (d);

wherein at least one of $R^3$ and $R^4$ represents an acyl residue of formula —CO—(CH$_2$)$_p$—CH(OH)R$^5$ of group (d);

wherein at least one of $R^3$ and $R^4$ represents an acyl residue of formula —CO—(CH$_2$)$_p$—CH(OR$^9$)R$^5$ of group (d);

wherein at least one of $R^3$ and $R^4$ represents an acyl residue of formula —CO—(CH$_2$)$_q$—N$^+$(R$^8$)$_3$Y$^-$ of group (d);

wherein at least one of $R^3$ and $R^4$ represents an acyl residue of formula —CO—(CH$_2$)$_q$—NH—COR$^9$ of group (d);

wherein at least one of $R^3$ and $R^4$ represent an acyl residue of formula —CO—NH—(CH$_2$)$_q$—COOR$^5$.

wherein at least one of $R^3$ and $R^4$ represents an acyl residue of formula —CO—NH—(CH$_2$)$_q$H of group (e);

wherein at least one of $R^3$ and $R^4$ represents an acyl residue of formula —CO—NH—(CH$_2$)$_q$—C$_{1-6}$-alkyl of group (e);

wherein at least one of $R^3$ and $R^4$ represents an acyl residue of formula —CO—NH—(CH$_2$)$_q$—COOC$_{1-6}$-alkyl of group (e).

Finally, the present invention provides compositions comprising at least one of curcuminoxazolide and of the new curcumin derivatives defined above, animal feed additives on the basis of such new curcumin derivatives and animal feed containing as an additive such new curcumin derivatives or compositions.

The acyl groups of the curcumin derivatives according to the present invention are derived from organic and inorganic acids which are physiologically acceptable.

Among the new curcumin-acylates, desmethoxycurcumin-acylates and bisdesmethoxycurcumin-acylates summarized under formula I the curcumin-acylates are the preferred group and in each group compounds with $R^3=R^4$ are again preferred.

Aliphatic acids can be straight or branched chain, saturated or unsaturated monocarboxylic acids which may be substituted by cyclic hydrocarbon groups such as phenyl, cyclohexyl or cyclohexenyl or by heterocyclic groups. Dicarboxylic acids should be monoesterified, tricarboxylic acids diesterified (esterified with a $C_{1-6}$-alkanol), e.g. mono methyl or ethyl esters of oxalic, succinic or maleic acid and diethyl or dimethyl esters of citric acid. Saturated straight and branched chain monocarboxylic acids may have 1-20 carbon atoms, such as formic, acetic, propionic, isopentanoic, hexanoic, decanoic, tetradecanoic, hexadecanoic, octadecanoic or 3,7,11,15tetramethylhexadecanoic (=phytanic) acid. Corresponding unsaturated carboxylic acids with one or more double or triple bonds may have 3-22 carbon atoms such as acrylic, crotonic, 2,4-hexadienoic cinnamic, myristoleic, palmitoleic, oleic, α-linolenic, δ-linolenic, linoleic, arachidonic, eicosapentaenoic (EPA), docosapentaenoic (DPA), and docosahexaenoic (DHA) acid. A group of preferred interest are polyunsatured aliphatic monocarboxylic acids (PUFAs) of the ω-3 and ω-6 family. Naturally occurring saturated and unsaturated carboxylic or fatty acids, especially when isolated from e.g. plant and animal oils by hydrolysis from glycerides can be used not only when separated from each other and highly purified but also as mixtures, in more or less purified and stabilised form of arbitrary composition so that mixtures of correspondingly acylated curcumins are obtained. Such mixtures can be used without further separation and/or purification according to the present invention.

Examples of saturated and unsaturated aliphatic di- or tricarboxylic acids with up to ten carbon atoms are oxalic, malonic, succinic, glutaric, pimelic, sebacic, maleic, fumaric, citraconic, mesaconic and citric acid used as their monoesters (dicarboxylic acids) or diesters (tricarboxylic acids). Aromatic acids may be monovalent, divalent or trivalent acids which can have from 5 to 20 carbon atoms and comprise carbocyclic or heterocyclic monocylic or fused ring systems. The heterocyclic ring systems may contain one or more heteroatoms selected from oxygen, sulfur and nitrogen. Examples of aromatic acids are benzoic acid and acylated hydroxy benzoic acids, furoic, thenoic, and 2-, 3- or 4-pyridinecarboxylic acid.

Araliphatic acids of preferred interest are phenyl acetic acid, mandelic acid and its $C_{1-4}$-acylates as well as p-methoxy-mandelic acid and its $C_{1-4}$-acylates. As in case of aliphatic acids di- or trivalent aromatic acids are mono- or diesterified, respectively, with a $C_{1-4}$-alkanol.

The aliphatic and aromatic acids mentioned above may be substituted by reactive groups such as amino, hydroxyl and/or oxo groups to form amino acids, hydroxy or oxo acids. Specific groups among such substituted acids are α-, and β-amino acids, especially the naturally occurring α-amino acids, keto acids, such as pyruvic and ketoglutaric acid, and aliphatic and aromatic hydroxy acids. Examples of aliphatic hydroxy acids are lactic, malic, citric and sugar acids, viz. glyconic, glycuronic and glycaric acids, such as D gluconic, D-glucuronic and galactaric (or mucic) acid. Examples of aromatic hydroxy acids are phenolic acids with one, two or three hydroxy groups, like o-, m-, p-hydroxy benzoic acid, p-coumaric, caffeic, and ferulic acid.

Amino groups present in acyl residues can be modified by acylation, while hydroxy groups present in acyl residues can be modified by, e.g. esterification or etherification. The resulting modified acyl groups are encompassed by the term "acyl derivatives" used in connection with the present invention.

Examples of $C_{1-4}$- or $C_{1-6}$alkyl groups representing residues $R^8$, $R^5$ and $R^7$, respectively, are methyl, ethyl, propyl, n-butyl, iso-butyl, tert.-butyl, pentyl and hexyl. The term $C_{1-5}$-alkanoyl is understood to define a $C_{1-4}$-alkyl-carbonyl group. Among $C_{1-12}$-alkyl groups $C_{1-4}$-alkyl groups are preferred.

The term alkali metal relates to Li, Na and K, while the term alkaline earth metal means Mg and Ca. The term anion of an inorganic acid relates to the anions of sulfuric acid, sulfuric acid monomethylester, methanesulfonic acid and hydrogen halogenides, i.e. $1/2SO_4^-$ or $MeOSO_3^-$ or $MeSO_3^-$ and Hal$^-$. Hal$^-$ represents Cl$^-$, Br$^-$ and J$^-$.

The acyl derivatives of the present invention as far as not known and described how to be prepared can be manufactured according to methods known per se for the esterification of phenolic hydroxy groups. Therefore, curcumin, desmethoxycurcumin or bisdesmethoxycurcumin is reacted with the corresponding acid RCOOH as such, its acid chloride RCOCl or acid anhydride (RCO)$_2$O.

In the case of esterification with an acid chloride or acid anhydride, the reaction is generally conducted in an inert solvent and in the presence of an organic base. As the solvent (which may instead act as a dispersion medium in the case of suspension rather than solution) there is conveniently used a lower halogenated hydrocarbon, e.g. methylene chloride or chloroform; a lower aliphatic or cyclic ether, e.g. diethyl ether, or tetrahydrofuran or dioxane, respectively; an aromatic hydrocarbon, e.g. toluene; or a lower aliphatic ketone, e.g. acetone. The base is suitably a lower trialkylamine, e.g. triethylamine; pyridine; or a di-(lower alkyl)-aminopyridine, e.g. dimethylaminopyridine. The molar ratio of curcumin: acid chloride or acid anhydride:base is conveniently in the range of 1:1-6:2-10 depending upon whether mono or diacyl derivatives are desired. In the case of the preferred diacyl derivatives an excess, i.e. more than two mol equivalents of the acylating agent is recommended. Moreover, the esterification is generally conducted in a temperature range from about −11° C. to about +100° C., preferably from about 0° C. to about 60° C., and most preferably from about 20° C. to about 40° C. Under such conditions the esterification is generally complete within about 1 to 24 hours, usually within about 2 to 6 hours, from the start of the reaction. It has been found to be advantageous to effect the esterification under an inert atmosphere, preferably using nitrogen or argon as the inert gas. Furthermore, where the base triethylamine is employed, it has been found to be advantageous in the case of particularly slow reactions to augment said base with up to about 20% of its molar amount of 4-dimethylaminopyridine.

Where the acid itself is used to esterify the curcumins, the conditions are generally similar to those employed for esterifications with an acid chloride or anhydride in respect of the solvent/dispersion medium and reaction temperatures. However, in this case a dehydrating agent is generally employed instead of a base. A particularly suitable dehydrating agent is dicyclohexylcarbodiimide optionally in the presence of an esterification catalyst such as N-hydroxybenzotriazole. The molar ratio of cucurmin:carboxylic acid:dehydrating agent: esterification catalyst is conveniently in the range of 1:1-6: 1-7:0-1. Esterifications using the appropriate carboxylic acid are generally complete within a few minutes up to about 18 hours.

In all these cases the product, i.e. the curcumin acyl derivative of formula I, can be isolated and purified by methods known per se, e.g. by adding a solvent such as methanol to induce the separation of the crude product from the mixture after reaction, chromatography and/or crystallization of the collected crude product.

The curcumin-borate derivatives of formula IB and IC, e.g., borate-citrate-curcumin and dicurcumin-borate-sulfate, can be prepared as described by H. J. Roth et al., Archiv der Pharmazie 297, 660-673 (1964) or in an analogous manner.

The acyl derivatives of the present invention and compositions containing them improve the performance of animals, viz. their general health status and during breeding their weight gain. The derivatives of the present invention can especially be regarded as modulators of the gastrointestinal microflora of the animals which is of importance for their health status including weight gain. Positive effects with this respect of the curcumin acyl derivatives of the present invention may be based at least partially, on their inhibitory effects on potentially pathogenic microorganisms, e.g. on antibacterial activity. Therefore, they can be used as feed additives or for the preparation thereof and of feed by mixing or processing them with conventional animal feed or components thereof for all kinds of animals in amounts to provide the required or desired daily uptake. Animals which may be in need of such additives comprise mammals, e.g. ruminants, pigs, calves, horses, pets, birds, e.g. poultry (chickens, hens, geeze, ducks, turkeys), fish and zoo animals. A group of animals for the breeding of which the present acyl derivatives are preferably useful are stock animals.

The normal daily dosage of a compound of formula I provided to an animal by feed intake depends upon the kind of animal and its condition. Normally this dosage should be in the range of from about 50 to about 1000 mg, preferably from about 100 to about 500 mg compound per kg of feed.

Correspondingly concentrated compositions for application in animals and the preparation of feed additives and feed can be prepared in accordance with methods well-known in the art.

The compounds of formula I can, however, also be administrated to animals in want thereof in the form of pharmaceutical preparations, especially for veterinary use.

The preparation of the acyl derivatives of the present invention is illustrated in more detail by the following Examples.

Example 1

To a solution of 3.68 g curcumin (10 mmole) in 10 ml tetrahydrofuran and 10 ml pyridine was slowly added at 0° C. a solution of 7.47 ml palmitoylchloride (24.7 mmole) in 30 ml of toluene. After additional stirring for 30 minutes at room temperature 20 ml water and 20 ml toluene were added and the mixture was stirred at 60° C. The water phase was separated and the organic phase was washed twice with water. The organic phase was evaporated to dryness and the solid residue crystallised from ethylacetate to yield 7.52 g curcumindipalmitate, m.p. 95-96° C.

Example 2

To a solution of 3.68 g curcumin (10 mmole) in 20 ml tetrahydrofurane and 5 ml pyridine were slowly added 10.2 ml of an approx. 2.5 molar solution of propionylformate in tetrahydrofuran. After stirring for 1 hour at 0° C., the mixture was added to 50 ml of water and extracted with ethylacetate. The organic phase was washed twice with water. The organic phase was evaporated to dryness and the solid residue crystallised from ethylacetate to yield 2.6 g of yellow crystals of curcumindiformate, m.p. 153-156° C.

Example 3

To a solution of 1.84 g curcumin (5 mmole) in 5 ml pyridine and 2.5 ml toluene was added at −50° C. a solution of 1.91 g phosphoroxichloride (12.5 mmole) in 2.5 ml toluene. The mixture was stirred for 3 hours at −40° C. The cold yellow suspension was added to a solution of acetonitrile and water at 0° C. The solution was made slightly alkaline by addition of 6 ml approx. 25% ammonium hydroxide solution. The solution was evaporated in the vacuum and the residue purified by chromatography on an RP-column with a water-acetonitrile-ammonium carbonate buffer. The product-containing fractions were collected and evaporated to dryness in the vacuum to yield 1.83 g of yellow crystals of curcumindiphosphate ammonium salt, m.p. 170-180° C. (dec.).

Example 4

To a solution of 3.68 g curcumin (10 mmole) in 20 ml pyridine were added in an inert atmosphere 3.98 g sulfurtrioxide/pyridine complex at room temperature. The mixture was stirred for 24 hours at room temperature. The solution was made slightly alkaline by addition of approx. 30 ml 2 n ammonium hydroxide solution. The solvents were evaporated in the vacuum. The residue was purified by chromatography on an RP column with water-acetonitrile-ammonium carbonate buffer. The product-containing fractions where collected and evaporated to dryness to yield 3.65 curcumindisulfate ammonium salt, m.p. 170-176° C. (dec.).

Example 5

To a suspension of 1.08 g L-lactic acid (12 mmole) in 20 ml dichloromethane and 1.09 g dihydropyran were added at 4° C. 40 mg p-toluenesulfonic acid. After complete dissolution of the lactic acid, 0.05 ml triethylamine followed by 1.95 g carbonyldiimidazole (12 mmole) were added at 0° C. After 1 hour of stirring at room temperature, 1.47 g curcumin (4 mmole) were added. After stirring for 24 hours, the mixture was diluted with acetonitrile and acidified by addition of 18 ml 2 n hydrochloric acid. After stirring at room temperature until complete deprotection the mixture was extracted with ethylacetate. The organic phase was washed with water. The organic phase was separated and evaporated to dryness. The residue was chromatographed on a silicagel column with toluene:acetone:acetic acid (85:13:2, v/v). The product-containing fractions where collected, evaporated and the residue crystallised from ethylacetate to yield 0.3 g curcumindilactate, m.p. 152-154° C.

Example 6

To a stirred mixture of 3.68 g curcumin (10 mmole), 4.04 g sorbic acid (36 mmole) and 0.1 g hydroxibenzotriazole hydrate in 20 ml tetrahydrofuran and 1 ml pyridine were added 4.95 g dicyclohexylcarbodiimide (36 mmole). After stirring the mixture for 24 hours at room temperature and 3 days at 40° C., the mixture was chromatographed on a silicagel column to yield 1.7 g of a raw product which after crystallisation from methylene chloride yielded 0.8 g of yellow crystals of curcumindisorbate, m.p. 228-232° C.

Example 7

To a solution of 3.68 g curcumin (10 mmole) in 20 ml tetrahydrofuran and 3 ml pyridine was slowly added at 0° C. a solution of 2.83 ml succinic acid monomethylesterchloride (23 mmole) in 5 ml of toluene. After stirring for 24 h at ambient, the reaction mixture was diluted with 100 ml acetic acid ethylester and washed with water. The organic phase was evaporated and the residue crystallised from ethyl acetate to yield 4.4 g curcumin-bis-methylsuccinate, m.p. 145-147° C.

Example 8

To a solution of 1.84 g curcumin (5 mmole) in 10 ml dichloromethane and 1.1 ml pyridine was added at 0° C. 2.38 g acetylsalicylchloride (12 mmole). After 2 h stirring at ambient the reaction mixture was diluted with 100 ml dichloromethane and washed two times with water. The organic phase was evaporated and the residue crystallised from diethyl ether to yield 3.0 g curcumin-bis-acetylsalicylate, m.p. 155°-162° C.

Example 9

To a solution of 1.84 g curcumin (5 mmole) in 5 ml tetrahydrofuran, 5 ml pyridine and 10 ml dichloromethane was added 1.42 g ethylisocyanoacetate (11 mmole). The mixture was stirred at ambient temperature for 7 days. The crystals where isolated by filtration to yield 1.72 g curcumin-bis-glycmethylestercarbamate, m.p. 198°-202° C.

Example 10

To a solution of 1.84 g curcumin (5 mmole) in 20 ml dichloromethane and 2.5 ml pyridine was added 1.34 g dimethylaminoglycine (13 mmole), 0.14 g 1-hydroxybenzotriazole (1 mmole) and 2.69 g dicyclohexcarbodiimide (13 mmole). The mixture was stirred for 24 h at ambient temperature. The solids where filtered off. The filtrate was evaporated in vacuum. The residue was slurried for 24 h in 20 ml diethyl ether. The solids where filtered off and dried in vacuum to yield 2.38 g curcumin-bis-dimethylglycinate, m.p. 135°-139° C.

Example 11

To a mixture of 0.54 g curcumin-bis-dimethylglycinate (1 mmole) and 5 ml dichloromethane was added 0.57 g methyljodide (4.mmole). After 24 h stirring at ambient temperature the solids where isolated by filtration to yield 0.58 g curcumin-bis-betainate diiodide, m.p. 150°-160° C.

Example 12

To a slurry of 1.85 g curcumin (5 mmole), 0.14 g 1-hydroxybenzotriazole (1 mmole) and 1.6 g N-formylaminobutyric acid in 5 ml pyridine and 50 ml dichloromethane was added 2.7 g dicyclohexylcarbodiimide (13 mmole). After stirring the mixture for 24 h at reflux, the solids were filtered off and washed thoroughly with dichloromethane. The filtrate was evaporated to yield 1.7 g curcumin-bis-formylaminobutyrate, m.p. 142-147° C. of approx. 80% purity.

Curcumin-bis-methylcarbonate can be prepared according to J. Milobedzka et al., Ber. Deutsche Chemische Gesellschaft 43, 2163-2170 (1910).

Curcumindiacetate, curcumindipropionate and curcumindibenzoate can be prepared according to U. Pedersen et al., Liebigs Ann. Chem. 1985, 1557-1569.

Dicurcuminborate hydrochloride can be prepared according to Z. Sui et al., Bioorganic & Med. Chem. 1, 415-422 (1993).

Curcuminisoxazolid can be prepared according to C. Selvam et al., Bioorganic & Med. Chem. 15, 1793-7 (2005).

Example 13

A piglet food containing borate-citrate-curcumin was prepared by mixing the following ingredients together using a conventional mixing apparatus at room temperature.

| Ingredient | Amount (kg) |
| --- | --- |
| Wheat | 32.6 |
| Maize | 18.7 |
| Rice | 5.0 |
| Wheat bran | 9.0 |
| Soybean meal | 23.0 |
| Soy oil | 2.0 |
| Wheat starch | 4.5 |
| Minerals * | 2.9 |
| Synthetic amino acids premix ** | 0.8 |
| Vitamins and trace elements premix *** | 1.0 |
| Borate citrate curcumin premix (10% in wheat starch) | 0.5 |

In principle the borate-citrate-curcumin premix may contain 1-20% of the curcumin derivative.

In Examples 13-15:
Sea salt, dicalcium phosphate and calcium carbonate;
Lysine, methionine and threonine;
Vitamins A, E, D3, K3, B1, B2, B6, B12, C, biotine, folic acid, niacin, pantothenic acid, choline chloride, copper sulphate, iron sulphate, manganese oxide, zinc oxide, cobalt carbonate, calcium iodide and sodium selenite.

Example 14

A growing pig food containing curcumin diphosphate ammonium salt was prepared by mixing the following ingredients together using a conventional mixing apparatus at room temperature.

| Ingredient | Amount (kg) |
| --- | --- |
| Soybean meal | 18.0 |
| Maize | 52.3 |
| Barley | 14.0 |
| Oat meal | 6.0 |
| Wheat bran | 5.2 |
| Soy oil | 2.0 |
| Minerals * | 1.5 |
| Synthetic amino acids premix ** | 0.5 |
| Vitamins and trace elements premix *** | 1.0 |
| Curcumin diphosphate ammonium salt premix (10% in wheat starch) | 0.5 |

In principle the curcumin diphosphate ammonium salt premix may contain 1-20% of the curcumin derivative.

Example 15

A broiler chicken food ("starter") containing curcumin di-[S]-lactate was prepared by mixing the following ingredients together using a conventional mixing apparatus at room temperature.

| Ingredient | Amount (kg) |
| --- | --- |
| Soybean meal | 34.50 |
| Maize | 20.00 |
| Wheat | 37.80 |
| Soy oil | 3.13 |
| Minerals * | 2.90 |
| Synthetic amino acids premix ** | 0.17 |
| Vitamins and trace elements premix *** | 1.00 |
| Curcumin di-[S]-lactate premix (10% in wheat starch) | 0.50 |

In principle the curcumin di[S]-lactate premix may contain 1-20% of the curcumin derivative.

Example 16

A broiler chicken food ("grower") containing curcumin di-betainate was prepared by mixing the following ingredients together using a conventional mixing apparatus at room temperature.

| Ingredients | Amount (kg) |
| --- | --- |
| Soybean meal | 31.2 |
| Maize | 20.0 |
| Wheat | 41.3 |
| Soy oil | 3.4 |
| Minerals * | 2.5 |
| Synthetic amino acids premix ** | 0.1 |
| Vitamins and trace elements premix *** | 1.0 |
| Curcumin di-betainate iodide premix (10% in wheat starch) | 0.5 |

In principle the curcumin di-betainate iodide premix may contain 1-20% of the curcumin derivative.

Evaluation of the Antimicrobial Activity of Curcumin Acyl Derivatives
Material and Methods
Derivatives of Curcumin Tested

| Number | Name of the derivative |
| --- | --- |
| 1 | Borate-citrate-curcumin |
| 2 | Curcumin diphosphate ammonium salt |
| 3 | Curcumin di-[S]-lactate |
| 4 | Curcumin di-betainate iodide |
| 5 | Dicurcumin borate chloride |
| 6 | Curcumin isoxazolid |

Bacterial Strains Used for the Tests

The following bacteria were isolated from pig gastrointestinal content: *Escherichia coli* 0.94 (A), *Escherichia coli* 0.96 (B), *Klebsiella pneumoniae* (C), *Salmonella typhimurium* pF3127 (D), *Salmonella enteritidis* pF1338 (E), *Enterococcus faecalis* (F), *Enterococcus faecium* (G), *Staphylococcus hyicus* (H), *Lactobacillus salivarius* (I) and *Lactobacillus acidophilus* 3 (J). Their identities were confirmed by microscopic examination after gram staining and biochemical testing using the appropriate API system. Test strains were maintained in tryptic soy broth (named BTS; Merck, Dammstadt, Germany) mixed with glycerol 25% (Sigma Chemical, Steinheim, Germany), frozen in liquid nitrogen and stored at −80° C. Overnight cultures of the test organisms were diluted in tryptic soy broth to the final concentration used for inoculation of the assay. Pure bacteria were counted on tryptic soy agar (Merck, Darmstadt, Germany) after aerobical incubation at 37° C. during 24 hours.

Measurement of the Antibacterial Activity

Borate citrate curcumin and curcumin diphosphate ammonium salt were dissolved in liquid agar (0.2%, heated at 50° C.) in sterile dry test tubes. Curcumin di-[S]-lactate and curcumin di-betainate iodide were dissolved in DMSO/water (50/50, v/v) in sterile dry test tubes. Sterilized nutrient broth was prepared using tryptic soy broth (Merck, Darmstadt, Germany), and 4.4 ml of it was added to each test tube. 500 µl of each of the dilutions and 100 µl of bacteria, diluted to the appropriate inoculum size ($2 \times 10^4$ to $10^5$ CFU/ml), was added to the test tubes. Final volume was brought to 5 ml. Dicurcumin borate chloride and Curcumin isoxazolid were preliminary dissolved in pure DMSO and then with tryptic soy broth (Merck, Darmstadt, Germany) to obtain a final concentration of DMSO of 5%. 200 µl of each of both last dilutions and 20 µl of bacteria, diluted to the appropriate inoculum size ($2 \times 10^4$ to $10^5$ CFU/ml), was added to sterilized 96-well plates (Falcon 353072 microtiter plates. Becton Dickinsin Labware, Meylan, France). The final concentration of each derivative was 1000M. The tubes and the microtiter plates were incubated during 24 to 48 hours (depending of the bacteria tested) at 37° C. and under agitation. Inhibition of growth was determined by bacterial counting after 24 hours of incubation. Subsequently the samples were serially diluted in 10-fold steps using sodium chloride peptone broth and all bacteria were counted on tryptic soy agar (Merck, Darmstadt, Germany), after aerobic incubation at 37° C. for 24 hours. All bacterial counts were realized with two replicate plates. In general, each assay was performed in two replicates.

Analysis of the Data

The reduction of bacterial growth was determined by subtracting the number of the bacteria of the test culture after 24 hours from the number of bacteria of the control culture. The colonies developed after incubation were counted, and the inhibitory effect was calculated according to Rico-Munoz and Davidson, J. Food Sci. 48, 1284-1288 (1983), using the following formula:

$$\% \text{ inhibition} = [1 - (T/C)] \times 100$$

wherein T is CFU/ml of test sample and C is CFU/ml of control.

The results are shown in Table 1.

TABLE 1

Percentage of inhibition of growth of bacterial strains A-J by curcumin derivatives (1-6), all tested at 1000 μM.

| | A | B | C | D | E | F | G | H | I | J |
|---|---|---|---|---|---|---|---|---|---|---|
| 1 | 62 ± 0.3 | 59 ± 17 | 12 ± 4 | 33 ± 29 | 14 ± 13 | 38 ± 34 | NT | −4 ± 42 | 2 se | NT |
| 2 | −11 ± 6 | −6 ± 0 | 22 ± 66 | 35 ± 12 | 35 ± 11 | 33 ± 9 | NT | 83 ± 1 | 7 se | NT |
| 3 | 35 ± 41 | 47 ± 28 | 25 ± 5 | 40 ± 72 | 30 ± 34 | NT | 13 ± 6 | 2 ± 7 | 64 ± 50 | NT |
| 4 | 36 ± 19 | 64 ± 12 | 30 ± 7 | 75 ± 11 | 28 ± 28 | NT | 29 ± 17 | NT | 100 ± 44 | NT |
| 5 | −2 ± 19 | −46 ± 32 | −70 ± 4 | 100 ± 238 | −1 ± 68 | 61 ± 149 | NT | 21 ± 89 | NT | 300 ± 104 |
| 6 | −65 ± 47 | −71 ± 20 | −87 ± 2 | −36 ± 80 | −19 ± 83 | −73 ± 14 | NT | −97 ± 4 | NT | −73 ± 28 | se = single evaluation for this assay,
NT = not tested

The invention claimed is:

1. A method of improving performance of animals comprising administering to an animal in need of performance improvement an animal feed which comprises a performance improving effective amount of an acyl derivative of curcumin, desmethoxycurcumin and bisdesmethoxycurcumin and of curcuminisoxazolide wherein the acyl derivatives are of the formula

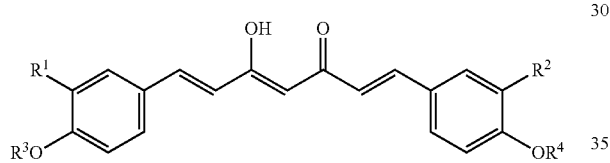

IA wherein $R^1$ and $R^2$ are different or the same and represent hydrogen or methoxy;

$R^3$ and $R^4$ are different or the same and at least one of them is an acyl residue selected from (a) sulfuric and phosphoric acid and salts thereof;

(b) an aliphatic, aromatic or araliphatic organic acid;

(c) formula $—CO—OR^5$,
with $R^5 = C_{1-6}$-alkyl;

(d) formula $—CO—(CH_2)_p—R^6$, $—CO—(CH_2)_q—N^{+(R^8)}{}_3 Y^-$, $—CO—(CH_2)_q—NH—COR^9$ or $—CO—NH—(CH_2)_q—COOR^5$,
with p=0 or 1,
q=an integer of 1-6
$Y^-$=an anion of an inorganic acid,
$R^6=—NHR^7$, $—NR^5 R^7$, $—CH(OH)R^5$ or $—C(OR^9) R^5$
$R^7$=H or $C_{1-6}$-alkyl
$R^8$=H or $C_{1-4}$-alkyl,
$R^9=C_{1-5}$-alkanoyl or (e) formula $—CO—NH—(CH_2)q—R^{10}$,
with $R^{10}$=H, $C_{1-6}$-alkyl or $—COOC_{1-6}$-alkyl;

the other being hydrogen if only one of $R^3$ and $R^4$ is acyl; or of the formula

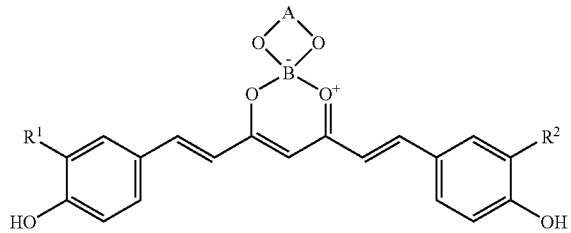

IB wherein $R^1$ and $R^2$ are as defined above, and

A is a group $—CO—CHR^9—CO—$ or $—CR^{10}R^{11}—CO—$
with $R^9$=H or $C_{1-4}$-alkyl,
$R^{10}$=H and
$R^{11}$=H, $C_{1-2}$-alkyl, $—[CH(OH)]_n—CH_2OH$,
$—(CH_2)_m—COOH$,
$—(CH_2)_m$-phenyl or $—CH(OH)—COOH$,
or $R^{10}=R^{11}=—CH_2—COOH$
or $R^{10}+R^{11}$=oxygen and
n and m=integers of 0-4; or
of the formula

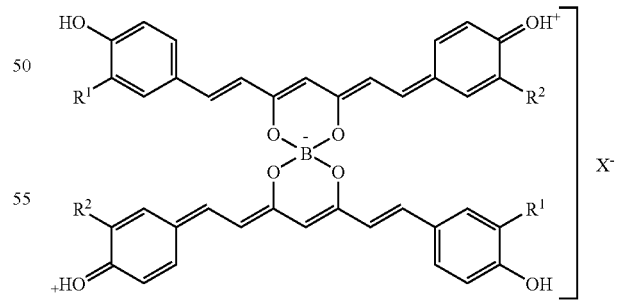

wherein $R^1$ and $R^2$ are as defined above and $X^-=OH^-$, $Cl^-$ or $HSO_4^-$.

2. A method as claimed in claim 1 wherein the acyl derivatives are of formula IA where $R^1$ and $R^2$ are methoxy.

3. A method as claimed in claim 1 wherein the acyl derivatives are of formula IA where one of $R^1$ and $R^2$ is methoxy and the other is hydrogen.

4. A method as claimed in claim 1 wherein the acyl derivatives are of formula IA where $R^1$ and $R^2$ are hydrogen.

5. A method as claimed in claim 1 wherein the acyl derivatives are of formula IA where $R^3$ and $R^4$ are the same.

6. A method as in claim 1, wherein the acyl derivatives are of formula IB.

7. A method as in claim 1, wherein the acyl derivatives are of formula IC.

8. A method according to claim 1, wherein the animal feed which comprises a performance improving effective amount curcuminisoxazolide.

9. A method according to claim 1, for improving the performance of animals, by modulating the gastrointestinal microflora of animals.

10. A method as defined by claim 8, wherein the animal feed comprises curcuminisoxazolide.

11. Acyl derivatives of curcumin, desmethoxycurcumin or bisdesmethoxycurcumin of formula

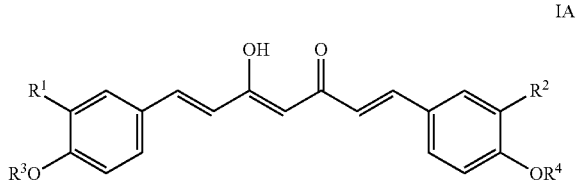

IA wherein $R^1$ and $R^2$ are different or the same and represent hydrogen or methoxy;

$R^3$ and $R^4$ are different or the same and at least one of them is an acyl residue selected from (a) phosphoric acid and salts thereof (b) an amino acid, a hydroxy-$C_{3-6}$— aliphatic acid or an aromatic or araliphatic acid;

(c) formula —CO—$OR^5$
with $R^5$=$C_{1-6}$-alkyl or (d) formula —CO—$(CH_2)_p$—$R^6$, —CO—$(CH_2)_q$—$N^+(R^8)_3Y^-$, —CO—$(CH_2)_q$—NH—$COR^9$ or —CO—NH—$(CH_2)_q$—$COOR^5$,
with p=0 or 1,
q=an integer of 1-6,
$Y^-$=anion of an inorganic acid,
$R^6$=—$NHR^7$, —$NR^5 R^7$, —CH(OH)$R^5$ or —CH($OR^9$)$R^5$,
$R^7$=H or $C_{1-6}$-alkyl,
$R^8$=H or $C_{1-4}$-alkyl,
$R^9$=$C_{1-5}$-alkanoyl or (e) formula —CO—NH—$(CH_2)_q$—$R^{10}$,
with $R^{10}$=H, $C_{1-6}$-alkyl or —$COOC_{1-6}$-alkyl;
the other being hydrogen if only one of $R^3$ and $R^4$ is acyl, with the proviso that when $R^1$ and $R^2$ are both methoxy $R^3$ and/or $R^4$ are not methoxycarbonyl, ethoxycarbonyl, glycyl, benzoyl or nicotinoyl.

12. Compositions comprising curcuminisoxazolide or an acyl derivative of curcumin, desmethoxycurcumin or bisdesmethoxycurcumin as claimed in claim 9.

13. Compositions comprising curcuminisoxazolide as claimed in claim 10.

14. Animal feed additives which comprise a composition as claimed in claim 12.

15. Animal feed additives comprising curcuminisoxazolide or compositions containing curcuminisoxazolide as claimed in claim 13.

16. Animal feed containing as an additive a compound or composition as defined in claim 11.

17. A method as claimed in claim 1 wherein the acyl derivatives are of formula IB in which R1=R2=methoxy, A =—C(R10)(R11)—CO— and R10=R11=—CH2—COOH.

18. Acyl derivatives of claim 11 wherein the acyl derivatives are of formula IB in which R1=R2=methoxy, A =—C(R10)(R11)—CO— and R10=R11=—CH2—COOH.

* * * * *